US005466583A

United States Patent [19]

Thomson et al.

[11] Patent Number: 5,466,583

[45] Date of Patent: Nov. 14, 1995

[54] METHOD AND APPARATUS FOR PERFORMING 3-DIMENSIONAL ANTIBIOTIC SUSCEPTIBILITY TESTS

[76] Inventors: Kenneth S. Thomson; Susan A. Thomson, both of 1282 S. 164th St., Omaha, Nebr. 68130

[21] Appl. No.: 694,438

[22] Filed: May 1, 1991

[51] Int. Cl.[6] .............................. C12Q 1/24; C12Q 1/18; C12M 1/26

[52] U.S. Cl. .......................... 435/30; 435/32; 435/287.1; 435/287.3; 435/288.3; 53/113; 53/474

[58] Field of Search ................................ 435/30, 32, 39, 435/292, 293, 299; 53/113, 474

[56] References Cited

U.S. PATENT DOCUMENTS

| | | | |
|---|---|---|---|
| 3,799,844 | 3/1974 | Campbell et al. | 435/292 |
| 3,892,632 | 7/1975 | Campbell et al. | 435/30 |
| 3,962,040 | 6/1976 | Campbell et al. | 435/291 |
| 4,273,877 | 6/1981 | Anagnostopoulos | 435/293 |
| 4,282,985 | 8/1981 | Yamamoto | 221/254 |
| 4,514,495 | 4/1985 | Schalkowsky et al. | 435/32 |

OTHER PUBLICATIONS

Product brochure: *Spiral System Instruments* 1990.

Product brochure: "Reduce the Cost of Microbial Assays" Spiral System Instruments, Inc.

*Journal of Antimicrobial Chemotherapy*—1984, 13, 45–54 "3–Dimensional Susceptibility T4sting of B–Lactam Antibiotics".

*Primary Examiner*—Robert J. Warden
*Assistant Examiner*—Theresa T. Snider
*Attorney, Agent, or Firm*—Zarley, McKee, Thomte, Voorhees & Sease; Mark D. Frederiksen

[57] ABSTRACT

An apparatus for performing 3-dimensional antibiotic susceptibility tests includes a plate with culture medium thereon, the plate rotatably mounted to a support for selective rotation. A knife is located to cut a slit in the culture medium as the plate is rotated, with a dispensing stylus located to dispense inoculum into the slit formed by the knife. A wedge apparatus is mounted adjacent the plate with a wedge-shaped leg depending into the culture medium so as to compress the culture medium towards the center of the plate, to thereby force the walls of the slit together after the inoculum has been deposited within the slit. A method for performing modified 3-dimensional antibiotic susceptibility tests includes the step of uniformly spreading a test microorganism over the top surface of culture medium on a plate. A slit is then formed in the culture medium and a uniform stream of suspending medium with a test microorganism therein is dispensed in and along the length of the slit. At least one antibiotic disk is then placed on the culture medium adjacent the slit, and the medium is incubated as desired.

4 Claims, 2 Drawing Sheets

METHOD AND APPARATUS FOR PERFORMING 3-DIMENSIONAL ANTIBIOTIC SUSCEPTIBILITY TESTS

TECHNICAL FIELD

The present invention relates generally to methods for testing susceptibility of antibiotics, and more particularly to an improved method and apparatus for performing a susceptibility test which reveals information with respect to the susceptibility of a microorganism to the antibiotics as well as the ability of the microorganism to inactivate the antibiotics.

BACKGROUND OF THE INVENTION

Clinicians and veterinarians often select antibiotic therapies for infections on the basis of laboratory test results. The laboratory tests, known as antimicrobial or antibiotic susceptibility tests, determine the inhibitory activity of antibiotics against the microorganisms that cause infections. If the antibiotic susceptibility test indicates that an antibiotic is sufficiently potent to treat an infection, the microorganism causing the infection is reported to be "susceptible" to the antibiotic. If the test indicates a lack of sufficient antimicrobial potency for successful therapy, the microorganism is reported as "resistant" to the antibiotic. In some tests other categories of susceptibility may also be reported, e.g. "moderate susceptibility" or intermediate susceptibility."

A problem with currently available antimicrobial susceptibility tests is their failure to reliably predict the outcome of therapy. Sometimes an antibiotic will fail to cure an infection even though the microorganism is susceptible to the antibiotic in the laboratory test. That is, the current routine laboratory tests can be misleading and give an over-optimistic impression of the therapeutic potential of antibiotics. These tests can therefore cause patients to be given ineffective treatments. In serious infections, this inadequacy of current laboratory tests can have fatal consequences.

There are many explanations for failures of antibiotic therapies that were initiated on the basis of antibiotic susceptibility tests. Some involve patient-related factors and are idiosyncratic for certain types of patients or infections. However one explanation is error arising from a deficiency in the antibiotic susceptibility test itself. The antibiotic susceptibility tests that are currently in routine use do not adequately detect the antibiotic-inactivating potential of some microorganisms. Some microorganisms produce enzymes that inactivate antibiotics. Such enzymes, which are not reliably detected in routine antibiotic susceptibility tests, may cause sufficient antibiotic inactivation at the infective site in a patient to cause a treatment failure. The currently used antibiotic susceptibility tests, which measure only the antimicrobial activity of antibiotics and not the ability of microorganisms to cause antibiotic inactivation, fail to take into account this very important determinant of the outcome of therapy. This deficiency in the tests places clinicians at a disadvantage in selecting the most appropriate antibiotic for their patients.

It is therefore a general object of the present invention to provide an improved method and apparatus for performing 3-dimensional antibiotic susceptibility tests.

Another object of the present invention is to provide a method for performing an antibiotic susceptibility test which provides information about both the antimicrobial activity of an antibiotic and the ability of microorganisms to inactivate antibiotics.

A further object of the present invention is to provide an apparatus for performing a 3-dimensional susceptibility test which will distribute a uniform amount of inoculum into an agar plate.

Still a further object of the present invention is to provide an apparatus for performing a 3-dimensional susceptibility test which will deposit inoculum into a slit in agar on a test plate.

Yet a further object is to provide an apparatus for performing a 3-dimensional antibiotic susceptibility test which is simple to operate.

These and other objects will be apparent to those skilled in the art.

SUMMARY OF THE INVENTION

The apparatus for performing 3-dimensional antibiotic susceptibility tests of the present invention includes a plate with culture medium thereon, the plate rotatably mounted to a support for selective rotation. A knife is located to cut a slit in the culture medium as the plate is rotated, with a dispensing stylus located to dispense inoculum into the slit formed by the knife. Preferably, the dispensing stylus is connected directly to the knife to deposit inoculum as the plate is rotated and the slit is formed. A wedge apparatus is mounted adjacent the plate with a wedge-shaped leg depending into the culture medium so as to compress the culture medium towards the center of the plate, to thereby force the walls of the slit together after the inoculum has been deposited within the slit. The method for performing modified 3-dimensional antibiotic susceptibility tests of the present invention includes the step of uniformly spreading a test microorganism over the top surface of culture medium on a plate. A slit is then formed in the culture medium and a uniform stream of suspending medium with a test microorganism therein is dispensed in and along the length of the slit. At least one antibiotic disk is then placed on the culture medium adjacent the slit, and the medium is incubated as desired.

DESCRIPTION OF THE PREFERRED EMBODIMENT

Figure 1:
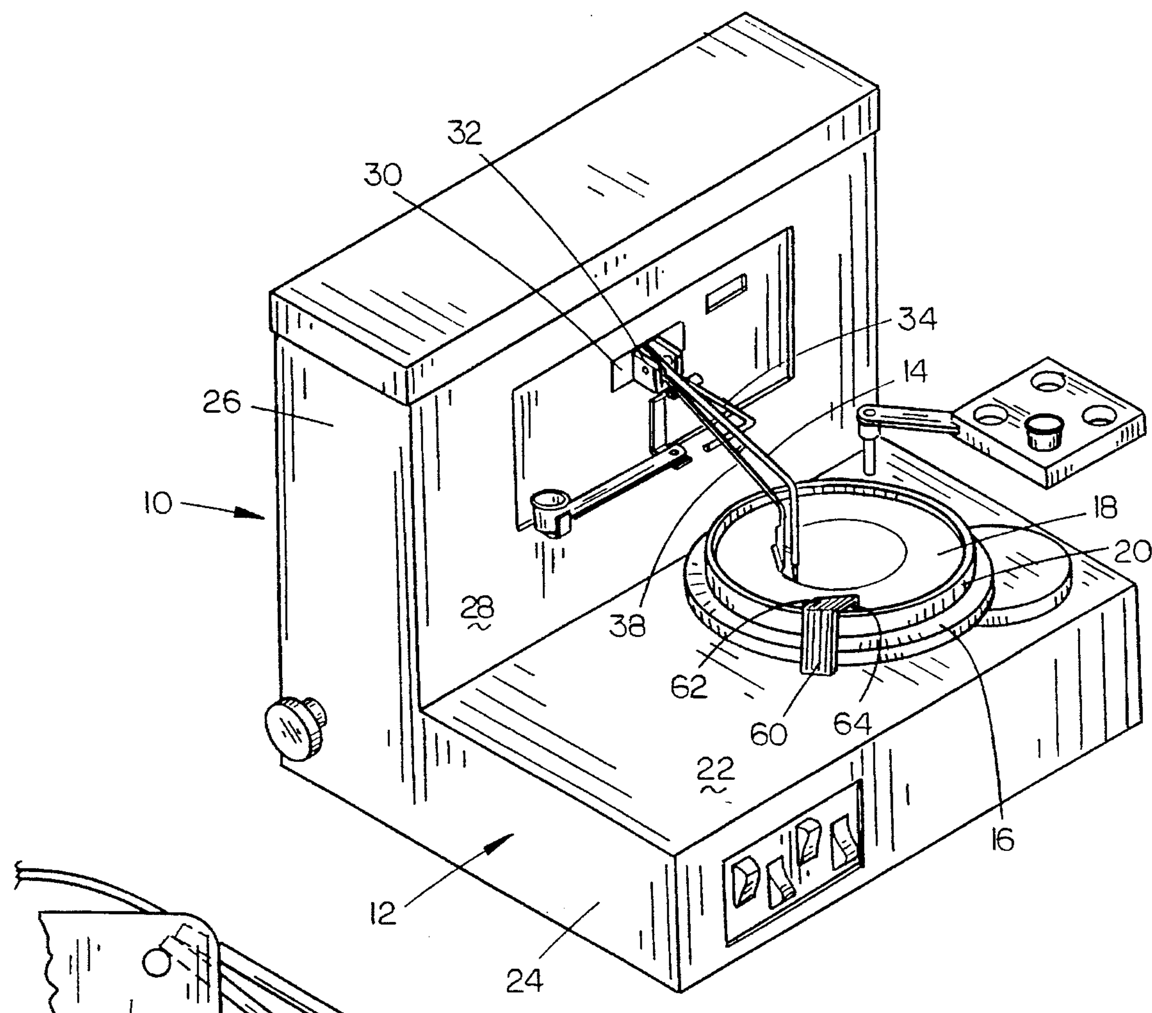
FIG. 1 is a perspective view of the testing apparatus of the present invention.

Referring now to the drawings, in which similar or corresponding parts are identified with the same reference numeral and more particularly to FIG. 1, the 3-dimensional antibiotic testing apparatus of the present invention is designated generally at 10 and includes a dispenser 12 from which projects a dispensing stylus 14 over a rotatable disk 16. Dispensing stylus 14 will dispense inoculum into agar 18 on a disk shaped plate 20, as described.

Dispenser 12 may be a conventional plater apparatus, such as that manufactured under the brand name SPIRAL PLATER™ by Spiral System Instruments, Inc. of Bethesda, Md. Dispenser 12 includes a rotatable disk 16 mounted on the top surface 22 of a base portion 24 of the dispenser 12. A motor (not shown) in the housing will rotate the disk 16 as desired. A petri dish or other conventional plate 20 will contain a culture medium (hereinafter referred to as agar) 18 on top of disk 16 for rotation therewith.

An upright portion 26 of dispenser 12 has a forward wall 28 adjoining top surface 22. Dispensing stylus 14 projects forwardly from upright portion 26 through a horizontal opening 30 in forward wall 28. Dispensing stylus 14 is a generally rigid tube which is pivotally connected at its upper end to a bracket 32 projecting from opening 30. Bracket 32 is horizontally movable within opening 30, for a purpose described herein below.

Dispensing stylus 14 is vertically supported by a projecting arm 34 which projects forwardly through forward wall 28 of upright portion 26. Arm 34 is pivotally mounted so as to raise and lower dispensing stylus 14 when arm 34 is pivoted.

Figure 2:
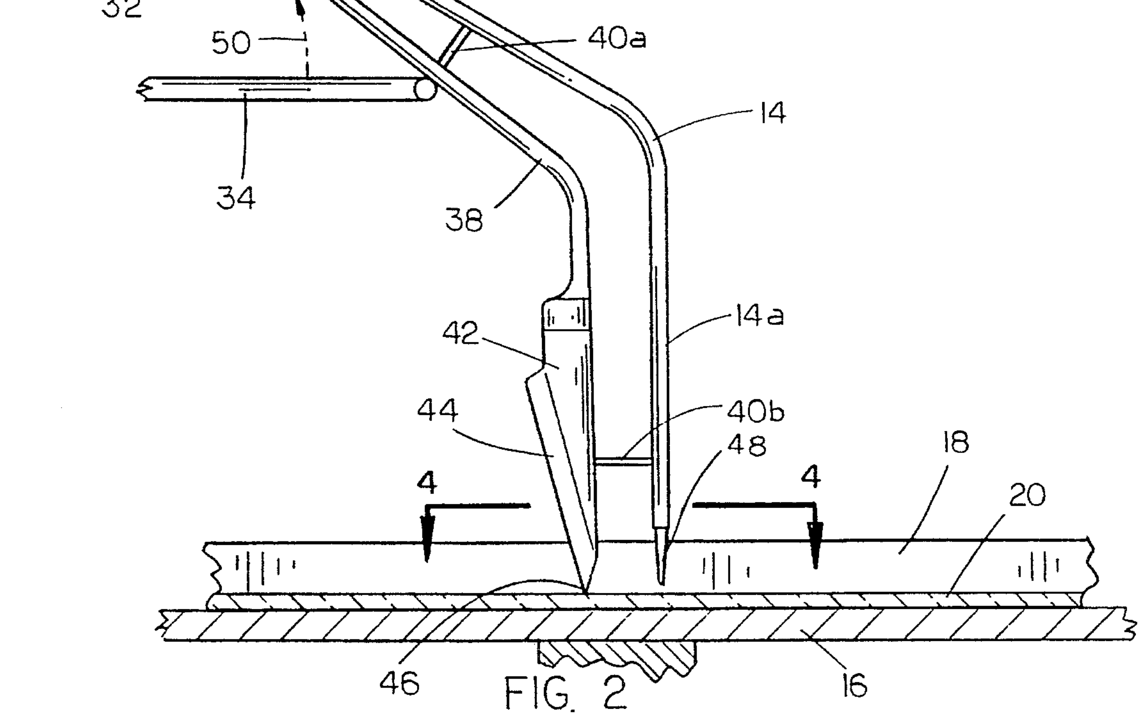
FIG. 2 is an enlarged side elevational view of the scalpel and dispensing tube oriented on an agar plate.

Referring now to FIG. 2, a knife 38 is mounted to the lower end **14*a* of dispensing stylus 14, using cross-members 40*a* and 40*b*. Knife 38 has a cutting blade 42 attached on the lower end thereof with a forward cutting edge 44 extending to the blade tip 46. Knife 38 is oriented on dispensing stylus 14 such that the knife is oriented vertically when the dispensing stylus is lowered to the position shown in FIG. 2. Dispensing stylus 14 has a dispensing tip 48 mounted at its lower end to dispense inoculum. As shown in FIG. 2, blade tip 46 will reach to the bottom of agar 18 but preferably is located slightly above plate 20 when stylus tip 48 extends downwardly into slit 52. The dispensing stylus 14 and knife 38 may be raised out of contact with agar 18 by pivoting arm 34 upwardly as shown by arrow 50 in FIG. 2**.

Figure 3:
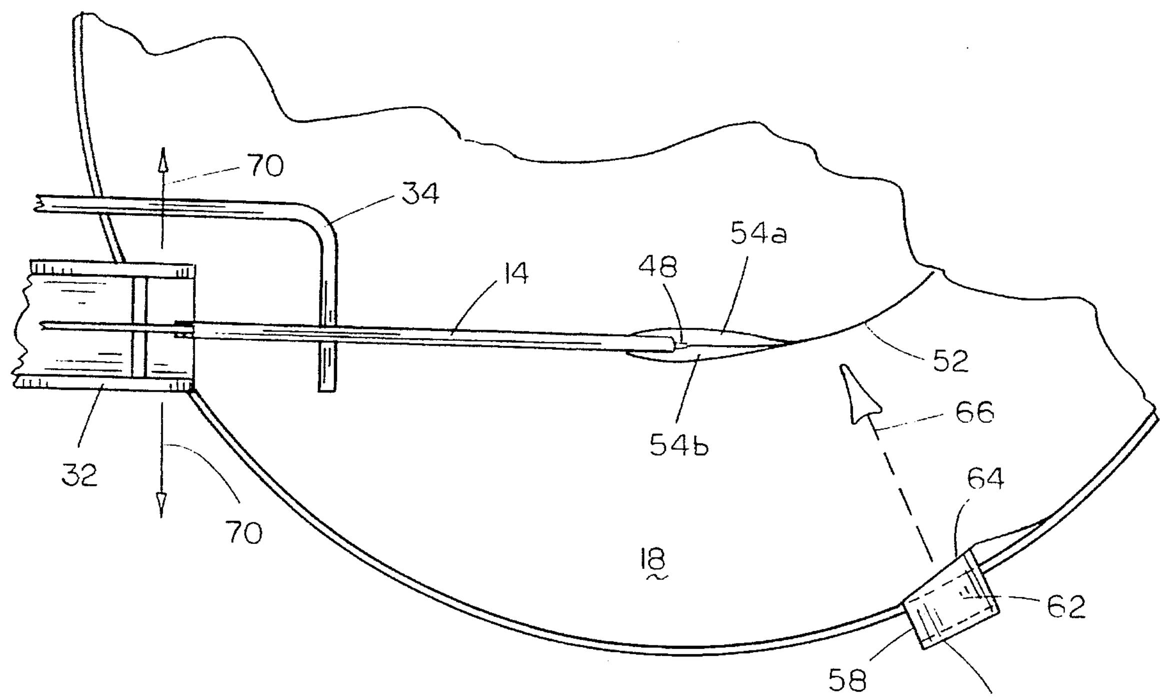
FIG. 3 is a top view of FIG. 2.
Figure 4:
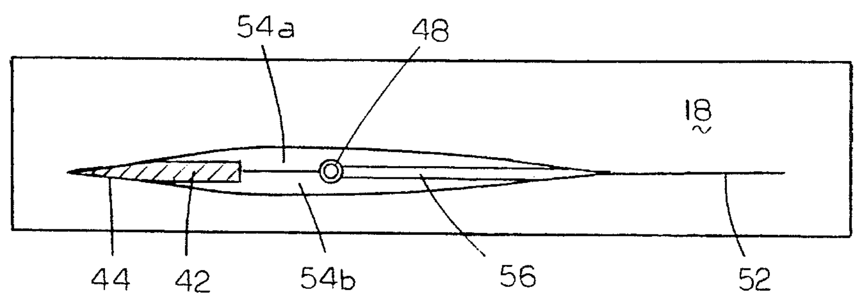
FIG. 4 is an enlarged sectional view taken at lines 4—4 in FIG. 2.

Referring now to FIGS. 3 and 4, a top view of the invention shows knife blade 42 cutting a slit 52 into agar 18. Cutting edge 44 will form a pair of vertical walls **54*a* and 54*b* which are separated at their upper end to permit stylus tip 48 to pass within slit 52. Stylus tip 48 will dispense a fluid stream of inoculum 56 within slit 52. It is preferred that a number eleven scalpel blade is utilized for cutting blade 42 so as to cause vertical walls 54*a* and 54*b* to close back together again after inoculum 56 has been dispensed. However, the agar 18 must also be of the appropriate consistency to cause the readhesion of walls 54*a* and 54*b* as shown in FIGS. 3 and 4. If walls 54*a* and 54*b*** do not adhere to one another, diffusion of the antibiotics cannot occur across the slit.

In order to assist in the readhesion of walls **54*a* and 54*b*, a wedge apparatus 58 is provided along the circumferential edge of plate 20. Wedge apparatus 58 includes an upstanding support leg 60 extending upwardly from top surface 22 of base portion 24, as shown in FIG. 1. A horizontally extending arm 62 projects over the edge of disk 16 and plate 20 such that a wedge-shaped leg 64 depends into agar 18 adjacent the circumferential edge of plate 20. Wedge-shaped leg 64 is oriented to force agar 18 radially inwardly as shown by arrow 66 so as to apply a "squeezing" force to vertical walls 54*a* and 54*b* to close slit 52**.

In the method of this invention, a standard quantity of the causative microorganism is uniformly spread over the top surface of an agar plate, in the conventional manner for performing a disk diffusion test. However, before placing the antibiotic disks onto the surface of the agar, the agar is inoculated for the 3-dimensional test, as described hereinbelow.

Figure 5:
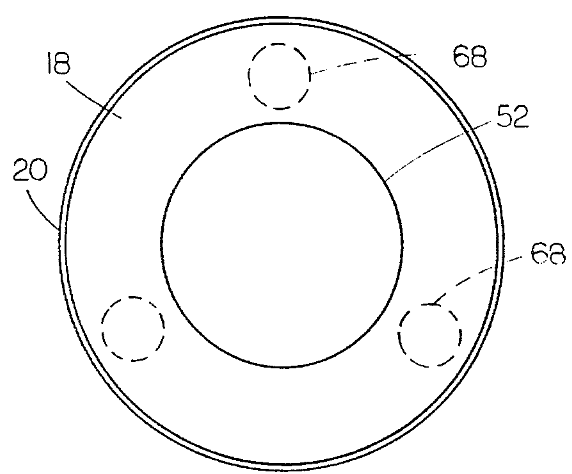
FIG. 5 is a top view of an agar plate showing a slit pattern in which inoculant is dispensed in the agar on the plate.

The inoculum is prepared by utilizing standard microbiological methods to make a suspension of the test microorganism in a sterile suspending medium (e.g. nutrient broth). However, the inoculum should be a heavier suspension than that used on the top surface of the agar. Preferably, the inoculum density should be at least $10^9$ cells per milliliter. The blade and stylus tip 42 and 48 are lowered into agar 18 while simultaneously rotating disk 16 and plate 20. Once the stylus tip 48 has reached the bottom of agar 18, the inoculum is dispensed within the slit 52 as the plate 20 is rotated. FIG. 5 shows the configuration of slit 52 after one full rotation of plate 20.

Once the test microorganism is deposited into the slit 52 in agar 18, several filter paper disks impregnated with specific concentrations of selected antibiotics are placed on the agar surface, as shown in broken lines in FIG. 5 by reference numeral 68. Preferably, conventional filter paper disks 68 are uniformly located 3 mm to one side of slit 52.

The agar is then incubated for an appropriate period. During incubation the antibiotics diffuse out of the disks into the agar in all directions and the microorganism grows along the slit of the agar as well as the surface of the agar, except in the areas where antibiotics inhibit its growth. Inhibition of growth is detected as clear zones of no growth on the agar around the antibiotic disks. The sizes of the inhibition zones are measured and compared to established interpretive criteria to determine the microorganism's susceptibility or resistance to the antibiotics. In addition to the standard susceptibility test, enzymatic inactivation of the antibiotics can be detected by inspecting the intersections of the inoculation within slit 52 with the margins of the inhibition zones. Antibiotic inactivation results in a distortion or discontinuity in the usually circular inhibition zone.

Figure 6:
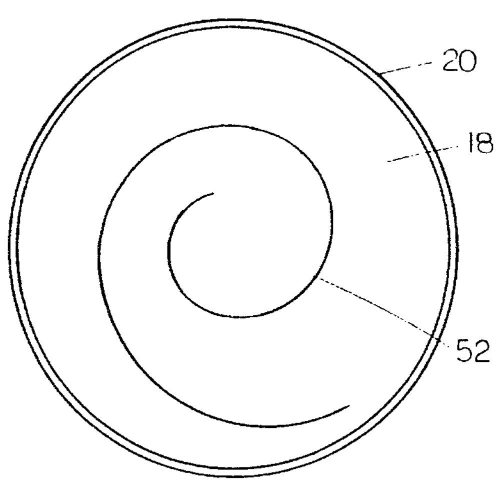
FIG. 6 is a view similar to FIG. 5, but showing a second slit pattern.

Modification of a conventional spiral plater enables the apparatus to form a lengthy slit 52 (as shown in FIG. 6) by shifting the knife and dispensing stylus radially as plate 20 rotates. The radial movement of dispensing stylus 14 is caused by the shifting of bracket 32 horizontally, as shown by arrows 70 in FIG. 3.

Whereas the invention has been shown and described in connection with the preferred embodiments thereof, it will be understood that many modifications, substitutions and additions may be made which are within the intended broad scope of the appended claims. For example, other apparatus for cutting the medium may be utilized, including lasers and the like. Similarly, a straight cut through a medium may be utilized as an alternative to the circular or spiral cuts described herein above. In addition, while it is preferred that the slit be formed to the bottom of the agar, it need not be that deep. Nor does the dispensing stylus necessarily need to be located at the bottom of the slit, since the inoculum will diffuse in the slit through capillary action.

There has therefore been shown and described an improved method and apparatus for performing 3-dimensional antibiotic susceptibility tests which accomplishes at least all of the above stated objects.

We claim:

1. An apparatus for performing 3-dimensional antibiotic susceptibility tests, comprising:

a plate for receiving and holding a culture medium;

a culture medium on said plate of sufficient quantity to cover said plate, said culture medium having a top surface, and a bottom surface in contact with the plate;

cutting means for cutting a slit having a pair of vertical walls in said culture medium, through the top surface of the culture medium;

means for moving said culture medium with respect to said cutting means to form a slit having a length in said culture medium;

an inoculum dispensing means for dispensing a uniform stream of inoculum into and along the length of said slit, having a dispensing end located so as to dispense inoculum into the formed slit;

means contacting the culture medium for forcing the vertical walls of the slit into abutting contact, rearwardly of the inoculum dispensing means.

2. The apparatus of claim 1, wherein said means for moving said culture medium includes:

a disk rotatably mounted on a support;

said plate supported on said disk for rotation therewith; and means on said support for rotating said disk.

3. The apparatus of claim 2, wherein said means for forcing the vertical walls of the slit together includes a wedge apparatus comprising:

an arm projecting from a support over the top surface of the culture medium; and a wedge-shaped leg depending from the arm and into the culture medium, oriented to compress the culture medium towards the center of the plate when the plate is rotated;

said wedge apparatus mounted independently of said plate and disk such that the culture medium will rotate with respect to the wedge apparatus.

4. A method for performing a modified 3-dimensional antibiotic susceptibility test, comprising the steps of:

uniformly spreading a standard quantity of causative microorganism over the top surface of culture medium on a plate;

forming a slit having generally vertical walls in the culture medium which extends from a first end to a second end and which extends downwardly through the top surface of the culture medium;

dispensing a uniform stream of suspending medium having a test microorganism therein, in and along the length of said slit between said vertical walls;

forcing the vertical walls of the slit together into abutting contact, such that the walls adhere to one another;

placing at least one antibiotic disk on the culture medium; and incubating the culture medium.

* * * * *